US007657445B1

(12) United States Patent
Goux

(10) Patent No.: US 7,657,445 B1
(45) Date of Patent: Feb. 2, 2010

(54) METHOD AND SYSTEM FOR MANAGING HEALTHCARE FACILITY RESOURCES

(75) Inventor: Timothy Gayle Goux, Mandeville, LA (US)

(73) Assignee: Rise Above Technologies, LLC, Mandeville, LA (US)

( * ) Notice: Subject to any disclaimer, the term of this patent is extended or adjusted under 35 U.S.C. 154(b) by 957 days.

(21) Appl. No.: 10/190,232

(22) Filed: Jul. 5, 2002

Related U.S. Application Data

(60) Provisional application No. 60/381,932, filed on May 20, 2002.

(51) Int. Cl.
*A61B 5/00* (2006.01)
*G06F 19/00* (2006.01)

(52) U.S. Cl. .................... 705/3; 705/2; 705/4
(58) Field of Classification Search ............ 705/2–4, 705/9
See application file for complete search history.

(56) References Cited

U.S. PATENT DOCUMENTS

| | | | | | |
|---|---|---|---|---|---|
| 4,453,732 | A | * | 6/1984 | Assanah et al. | 280/648 |
| 5,111,391 | A | * | 5/1992 | Fields et al. | 705/9 |
| 5,365,425 | A | * | 11/1994 | Torma et al. | 705/2 |
| 5,652,842 | A | * | 7/1997 | Siegrist et al. | 705/2 |
| 5,706,441 | A | * | 1/1998 | Lockwood | 705/3 |
| 5,765,140 | A | * | 6/1998 | Knudson et al. | 705/9 |
| 5,842,173 | A | * | 11/1998 | Strum et al. | 705/1 |
| 5,995,937 | A | * | 11/1999 | DeBusk et al. | 705/2 |
| 6,049,776 | A | * | 4/2000 | Donnelly et al. | 705/8 |
| 6,151,581 | A | * | 11/2000 | Kraftson et al. | 705/3 |
| 6,223,164 | B1 | * | 4/2001 | Seare et al. | 705/2 |
| 6,314,556 | B1 | * | 11/2001 | DeBusk et al. | 717/107 |
| 6,330,326 | B1 | * | 12/2001 | Whitt | 379/265.13 |
| 2001/0016821 | A1 | * | 8/2001 | DeBusk et al. | 705/2 |
| 2001/0051888 | A1 | * | 12/2001 | Mayhak et al. | 705/8 |
| 2002/0069001 | A1 | * | 6/2002 | Sinex | 701/29 |
| 2002/0099571 | A1 | * | 7/2002 | Waku et al. | 705/2 |
| 2002/0103691 | A1 | * | 8/2002 | Smith | 705/9 |
| 2002/0165735 | A1 | * | 11/2002 | Stangel | 705/3 |
| 2002/0184069 | A1 | * | 12/2002 | Kosiba et al. | 705/8 |
| 2003/0033184 | A1 | * | 2/2003 | Benbassat et al. | 705/8 |
| 2003/0061089 | A1 | * | 3/2003 | Weaver | 705/9 |
| 2003/0074222 | A1 | * | 4/2003 | Rosow et al. | 705/2 |
| 2004/0019504 | A1 | * | 1/2004 | Korom et al. | 705/2 |
| 2004/0039628 | A1 | * | 2/2004 | Thompson et al. | 705/9 |

OTHER PUBLICATIONS

Jerry Levesque. "Improving Patient Satisfaction With Time Spent In An Orthopedic Outpatient Clinic" Dec. 2000. Canadian Journal of Surgery. vol. 43, Iss. 6. p. 431.*

(Continued)

*Primary Examiner*—C. Luke Gilligan
*Assistant Examiner*—Neal R Sereboff
(74) *Attorney, Agent, or Firm*—Troutman Sanders LLP; James E. Schutz; Filip A. Kowalewski

(57) ABSTRACT

The present invention provides a method and system for managing resources of an enterprise, in particular a healthcare enterprise. One aspect of the present invention provides a method and system for remote access and exchange of information for managing enterprise resources using a distributed computing environment such as the Internet or World Wide Web. The system provides real-time management of healthcare facility resources including clinical hours provided per patient per day.

3 Claims, 16 Drawing Sheets

OTHER PUBLICATIONS

Lyle Byron Snider, Ph.D. "A Health Department Clinic Nurse-Staffing Model" 1993. The University of North Carolina at Chapel Hill.*

U.S. Appl. No. 60/209,107, filed on Jun. 2, 2000.*

Visual Staff Scheduler Pro Version 4 manual.*

NM REquirpement of LTC facilities, State Law 7.009.0002 dates included on sections.*

Puget Sound Behavioral Health Performance Review, Dec. 13, 2002.*

Crandall, Mary, "Nurse-to-Patient Ratios Addressing Concerns in Legislation" HealthCare advocate Apr./ May 2000.*

Mason, Elizabeth, "How to Write Meaningful Standards of Care" Delmar Publishing 1994.*

ExcelCare Promotional Materials, 1997.*

Various Webpages ExcelCare 1999.*

Harrington, Charlene et al., "Experts Recommend Minum Nurse Staffing Standards for Nursing Facilities in the United States" Gerontologist vol. 40, No. 15-16.*

Louisiana Standards for Payment for Nursing Facilities, 1996.*

* cited by examiner

Daily Census - Search

Community: DEMO COMMUNITY — 702

Entry Date: 5 - 7 - 02 (mm-dd-yy)

Submit

704

| Care Level | Census | Regulatory Required | Budget Hours | Actual Hours | Regulatory Set-PPD | Budget Set-PPD |
|---|---|---|---|---|---|---|
| Level 1 | 0 | | | | 2.35 | 2.7 |
| Level 2 | 0 | | | | 2.6 | 3 |
| Level 3 | 0 | | | | 4.5 | 4.5 |
| Level 4 | 0 | | | | 2.35 | 4 |
| TOTALS | 0 | 0 | | 0 | | |
| PPD | | 0 | 0 | 0 | | |

Monthly Summary and Projections

| | |
|---|---|
| Days/Month: | 30.42 |
| Month-To-Date Census: | 105 |

METHOD AND SYSTEM FOR MANAGING HEALTHCARE FACILITY RESOURCES

CROSS-REFERENCE TO RELATED APPLICATIONS

The is application claims benefit of priority to U.S. provisional application Ser. No. 60/381,932 filed on May 20, 2002, entitled "Method and System for Managing Healthcare Facility Resources."

BACKGROUND OF THE INVENTION

1. Field of the Invention

The present invention is directed to methods and systems for managing commercial enterprise resources, more particularly healthcare facility resources, most particularly for managing healthcare clinical hours provided per patient per day per facility, preferably per acuity/care level.

2. Related Art

National and local economies are rapidly blending into a single global economy. Fluctuations in prices in one geographic location inevitably affect prices in other geographic regions. Similarly, businesses having a local office and a few regional offices are transitioning into companies servicing an international market. As businesses grow and add additional offices or facilities, the entire enterprise becomes a series of interconnected offices.

Each office or facility of an enterprise can affect the overall performance of the enterprise. Thus, the allocation of resources in one unit can impact the commercial viability of a large enterprise. Typically, commercial enterprises budget resources to maximize profitability. Computer-based systems and procedures for budgeting and forecasting corporate performance and for monitoring and evaluating actual performance relative to budget or forecast are known in the art and include spreadsheet technology.

The process of budgeting enterprise resources can be an extensive and time consuming task. Large amounts of enterprise data are typically entered into a spreadsheet program such as Excel or Lotus 1-2-3 to generate a profit/loss analysis. Typically, the data used in these calculations is stale by at least a few days, more typically a few weeks. Also, as a result of the time lag between the data and the final data analysis, the current enterprise performance with regard to budget can only be estimated.

A further challenge to the effective management of any geographically dispersed organization is the timely exchange of, and access to, critical information. This challenge is particularly pronounced in the areas where regional regulations or recommended guidelines greatly impact resource allocations and the budget. Ideally, data collected in real time should be processed into the budget and available immediately. With the continued evolution of data communication, e.g., over the Internet and/or the World Wide Web, the infrastructure required to facilitate timely exchange and availability of data is generally available.

Despite exiting technology including spreadsheet-based systems and software programs, there is a need for a method and system for facilitating information exchange between individuals and entities of an enterprise for managing resources. In particular, there is a need for a method and system for managing resources in enterprises having at least two units wherein each unit is subject to different regulations or recommended guidelines. Additionally, a need exists for a system and method for managing resources in enterprises by remote information access and exchange, e.g., over a computer network such as the Internet and/or the World Wide Web, with reduced latency.

SUMMARY OF THE INVENTION

The present invention is directed to a method and system for managing commercial enterprise resources, more preferably healthcare facility resources, most preferably for managing healthcare clinical hours provided per patient per day per facility, preferably per acuity level as set by controlling authorities or by internal standards. One embodiment of the present invention provides a method and system for remote access and exchange of information for managing enterprise resources using a distributed computing environment such as the Internet, World Wide Web, intranet, wide area network, and local area network.

These and other objects, features, and advantages of the present invention will become more apparent upon reading the following specification in conjunction with the accompanying drawings.

BRIEF DESCRIPTION OF THE DRAWINGS

Figure 10B:
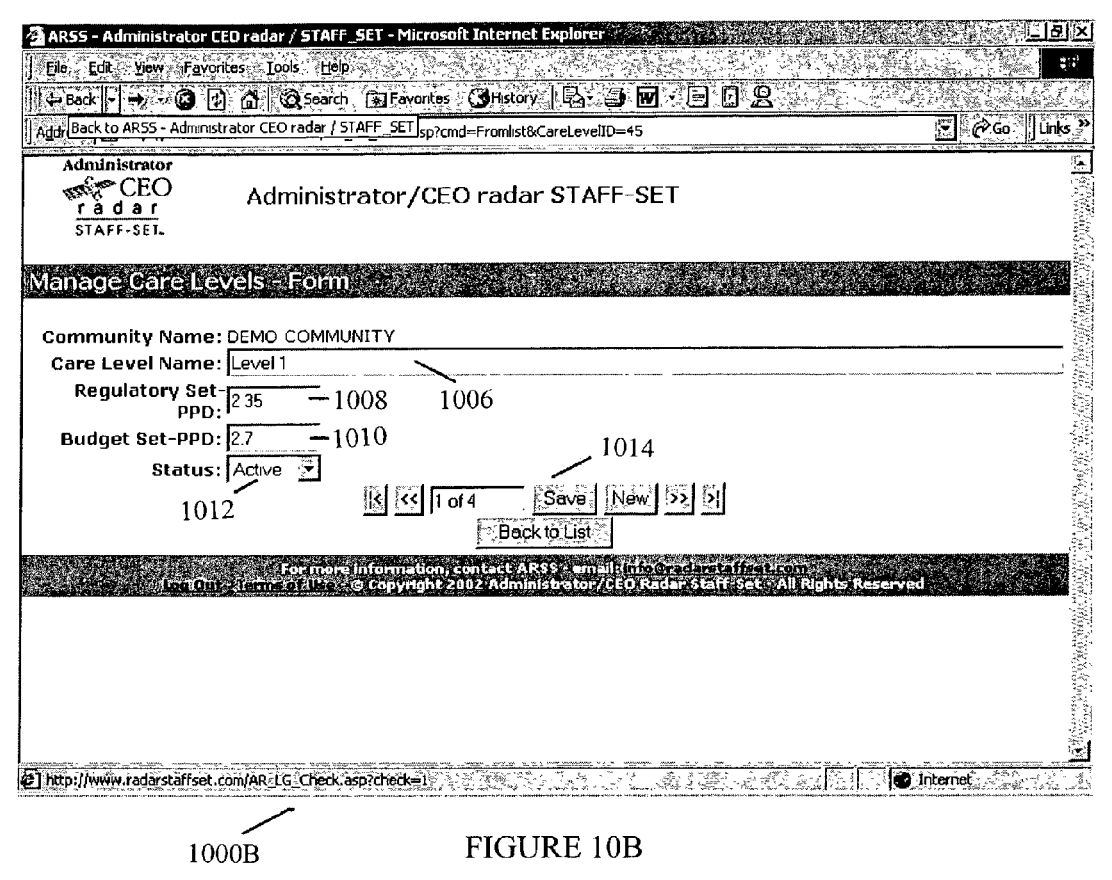
Figure 11B:
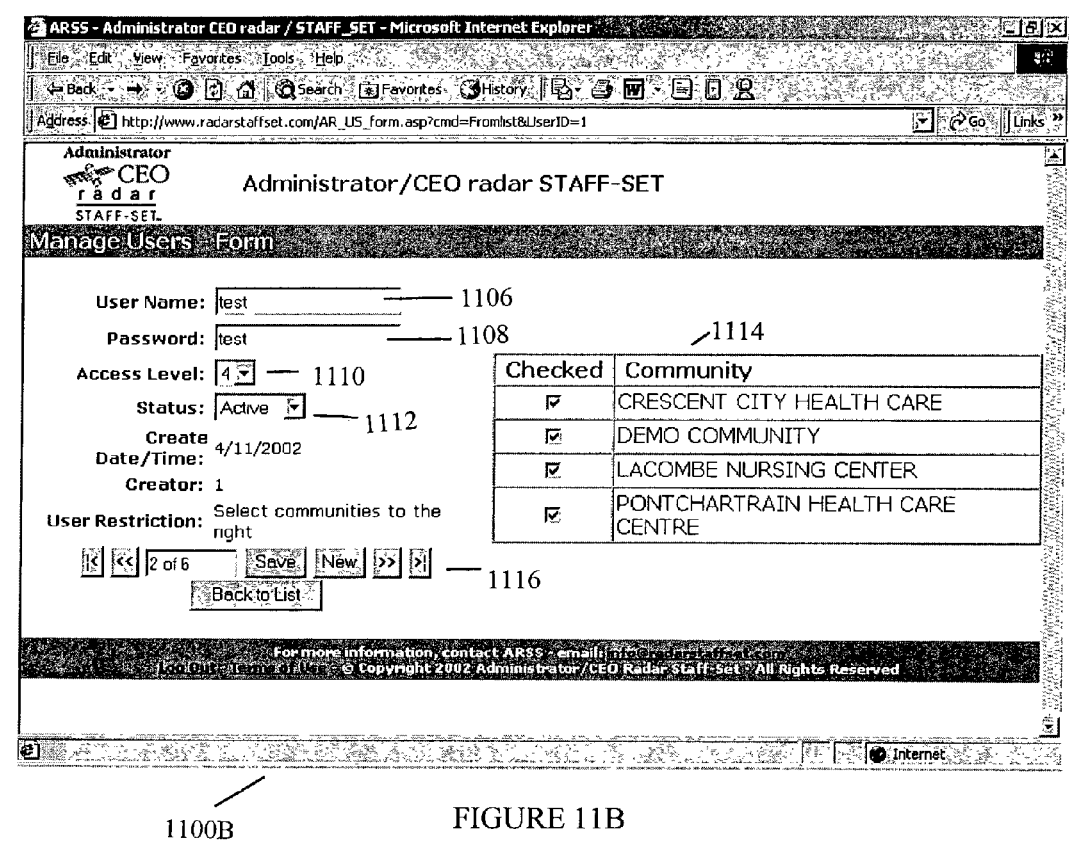

FIGS. 3-12 are representative user interface screens of an exemplary embodiment of the present invention.

DETAILED DESCRIPTION OF THE INVENTION

Figure 1:
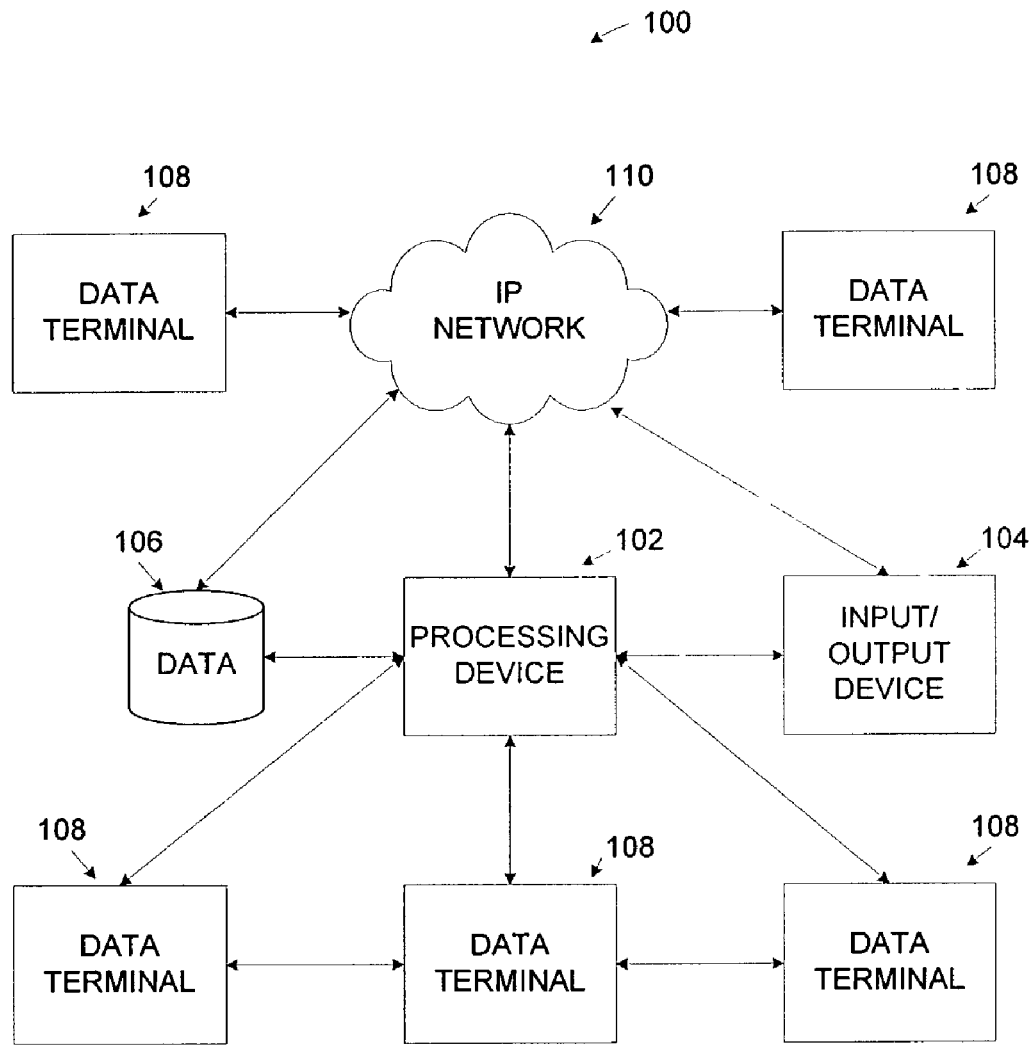
FIG. 1 is a functional block diagram illustrating a representative operating environment for an exemplary embodiment of the present invention.

The present invention provides a method and system for managing resources of an enterprise. An enterprise includes but is not limited to a group of at least one, preferably two or more economic units of an organization, preferably a commercial organization. The units can be offices, facilities, or branches. The present invention can be in communication with, include, or be otherwise be connected to an Internet Protocol (IP) network enabling the system to dynamically obtain, process, and communicate data between units or individuals, preferably in real-time. Alternatively, data can be exchanged using wireless communication technology, standard telephony technology, or via satellite or other conventional communications technology.

Another embodiment provides a method and system of managing resources in a healthcare enterprise. Although the invention will be generally described in the context of a healthcare enterprise, it will be appreciated that the enterprise can be any commercial enterprise. A healthcare enterprise includes at least one healthcare facility. A healthcare facility can include but is not limited to a hospital, nursing home, assisted living facility, medical center, hospice, or other facility for providing medical services or healthcare to patients. A healthcare enterprise can include units located in different geographic units, such as states, provinces, counties, parishes, countries, and nations. Each geographic region can have different sets of regulations including laws, statutes, codes, cannons, and guidelines for governing healthcare facilities. For example, one state may mandate a specific number of clinical hours be provided to a patient per day the patient is in a healthcare facility in that geographic region. Clinical hours refer to medical staff hours provided. Medical staff includes nurses, doctors, aids, nurse practitioners, nurse's aids, and other medical professionals. Another state may mandate a different number of clinical hours be provided to a patient having similar medical needs in that state. Thus, a large healthcare enterprise can have units in several geographic locations and each unit can be subject to different regulations. The regulations or guidelines can affect the management of resources because the regulations can require a specific amount of resources be allocated.

In an exemplary embodiment, clinical hours provided to a patient in a healthcare facility can be communicated to the system periodically, preferably daily (i.e., each 24 hour period), most preferably in real-time and processed by the system of the present invention. Communication of the data can be Web-enabled or can occur using conventional communication technology including telephone lines, wireless communication, satellites, radio, intranet systems etc. The system is operative to process the data and output the results of the data processing to a user. Data processing can be performed, at least in part, by a software module. A user can optionally load specific software into the system or customize the software according to specific needs. Data processing of the system includes but is not limited to budgeting facility resources, preferably salaries, most preferably clinical hours, even more preferably reimbursable salary hours.

Budgeting comprises comparing the actual clinical hours provided to a patient to the regulatory mandated or recommended number of hours required to be provided to the patient. Budgeting also comprises comparing actual clinical hours provided to the budgeted clinical hours for the patient of a facility. It will be appreciated that budgeting can be patient focused including patient acuity/care level, facility focused, or enterprise focus. Thus, total enterprise clinical hours can be compared, total hours of a single facility can be compared, and facility hours can be compared to other facilities. Another aspect of budget enables a user to compare clinical hours provided by category or level of care provided to a patient.

Clinical hours provided can be received by the system from user input. In one embodiment, data terminals 108 are located within each facility. Medical staff can input the clinical hours they provide to a patient using data terminal 108 or alternatively, an administrator can input the actual clinical hours data provided per facility. Data terminals 108 can include personal computers, pagers, telephones, wireless communication devices, or any other device operative to transmit data to the system. The system can also be in communication with a payroll system, manual or automatic, and electronically obtain clinical hours data from the payroll system.

Thus, an individual can obtain a real-time or near real-time analysis depending on the frequency of data transmission of clinical hours provided to patients within facilities of an enterprise, preferably facilities subject to differing regulatory requirements. The individual, preferably an officer of the enterprise, can then reallocated, adjust, or modify the budgeted resources of a facility or enterprise to meet regulatory standards and/or recommended standards while providing a predetermined level of care.

The method and system of the present invention can also provide an individual with enterprise resource management capabilities. Resources includes but are not limited to employees, employee salaries, staffing patterns, staffing hours, clinical hours and reimbursable items.

FIG. 1 is an exemplary functional block diagram illustrating a representative operating environment for an exemplary embodiment of the present invention. An enterprise resource management system 100 comprises one or more data terminals 108, one or more processing devices 102, an input/output device 104, a database 106, each coupled to an Internet Protocol (IP) network 110. Although FIG. 1 illustrates an operating environment including only a single processing device 102, those skilled in the art will appreciate that the operating environment of the resource management system 100 can include multiple processing devices 102 and databases 106. The IP network 110 represents a distributing computer network and can be implemented by the global Internet, a wide area network (WAN), or an enterprise-wide local area network (LAN). Data in the system can be received or transmitted using the IP network 110.

An exemplary processing device 102 can comprise an operating system, a Web server, an XML parser, and a user interface. The processing device 102 can be coupled to a database 106 comprising one or more configuration files to support processing operations. The platform of the processing device 102 is provided by the operating system which is preferably implemented by Microsoft Corporation's "WINDOWS 2000" or Sun Microsystem's "SOLARIS" operating systems. Although the "WINDOWS" and the "UNIX" platforms represent preferred platforms, it will be appreciated that processing device 102 can be supported by other operating systems and is not limited to those described herein.

A Web server can support Web-based communications with data terminals 108 and processing device 102 in a Web-enabled computing environment. The XML parser can accept messages and convert those messages to XML format for communication via the Web server. The XML parser also can extract information from an XML message received by the Web server and supply the extracted information for processing. The Web server also communicates with the user interface via application programming interfaces (APIs). The Web server is preferably implemented by an "XITAMI" server available from iMatix Corporation of Antwerpen, Belgium.

The processing device 102 supports the processing of enterprise data. APIs can be used to access functions supported by the processing device 102. The processing device 102 also can access configuration files maintained by the database 106 in support of processing functions. The configuration files typically contain descriptive information identifying characteristics of system components and data structures.

A user interface provides a mechanism for a user, such as an assistant administrator, to input information about the enterprise. Data terminals 108 can also comprise a user interface, and optionally a processing device 102. Data terminals 108 can be located in different geographical areas having geographic specific regulations applicable to the enterprise.

The system can manage a healthcare facility's medical provider payroll. The largest component of a healthcare facility's payroll is clinical hours, the hours medical professionals, including licensed nurses and certified nursing assistants provide to patients. Specific clinical hours are directly correlated to regulatory or recommended requirements for the operation of healthcare facilities. The present invention monitors, tracks, and processes enterprise data, periodically, preferably daily, most preferably hourly, even most preferably in real time. A user can adjust clinical hours in one or more facilities of an enterprise to meet regulatory mandated allocations of clinical hours or to exceed regulatory mandated clinical hours as budgeted.

Considering the regulatory or recommended requirements is very important to operate in an insurance reimbursable service industry. Materially exceeding regulatory or recommended amounts of clinical hours can significantly reduce profits of a healthcare facility because reimbursement is based on the clinical hours required for specific levels of care; therefore, verifying clinical hours periodically, preferably at least daily is advantageous to managing resources. For example, if a facility is over the required clinical hours by 60 clinical hours/per day, the monthly cost/loss to that provider will run $18,000, or over $200,000 annually.

Figure 2:
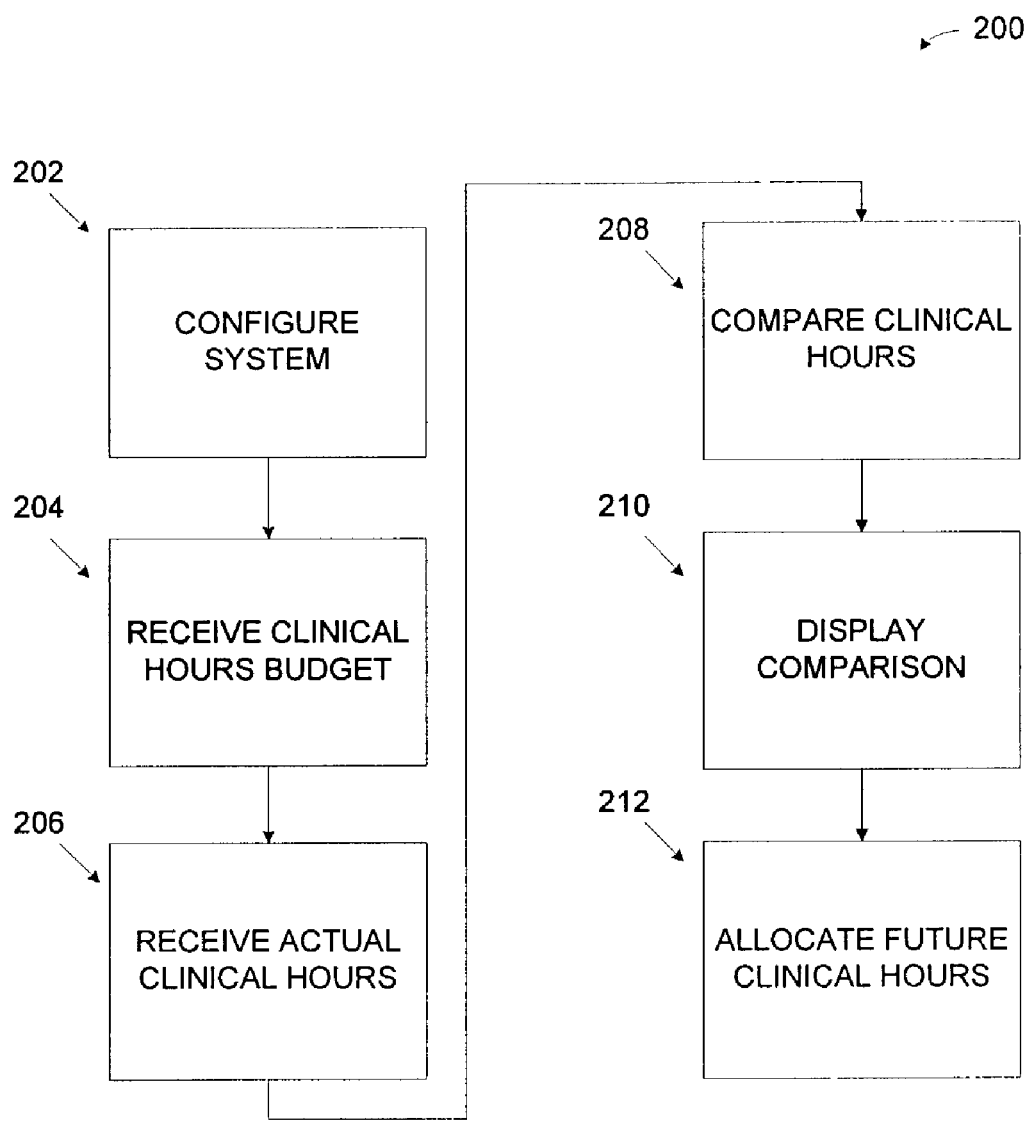
FIG. 2 is a functional block diagram of an exemplary process of an embodiment of the present invention.

FIG. 2 is a functional block diagram of an exemplary process 200 of the present invention. In step 202, the system receives configuration parameters from a user. Configuring the system involves setting the care/acuity levels (based on reimbursement, corporate policy), setting the clinical hours (a ppd per care level) for each care level based on desired budget allocations, setting the regulatory (or) recommended clinical hours per care level. The clinical hours that are associated with each care level are (by industry) standard referred to as a 'ppd', which stands for per patient day. Configuring system also refers to establishing levels of access for facility level personnel and corporate personnel. Access can be for one facility or multiple sites. The user can create or identify particular facilities of an enterprise or multiple enterprises. Once a facility is identified, the system can be customized to that facility. The user can input the geographic regulatory requirements or recommended guidelines per level of patient care for each facility. The regulatory requirements can be manually inputted by a user or they can be automatically loaded on the system when the user identifies the facility by geographical location and the type of facility. Geographical regulatory or recommended guidelines configuration files can be stored on processing device 102 or can be accessed from database 106. It will be appreciated that the term "regulations or regulation" includes geographical regulations such as state or federal regulations, county, municipal, province, parish or other governmental regulations, and recommended guidelines, industry standards, and trade associations recommendations. The system can also default to a preset value of clinical hours per level of care per patient. The term "required clinical hours" or "required hours" means the clinical hours budgeted, recommended according to guidelines, or required by regulations.

The system can be adapted to receive data for multiple Resident/Patient levels of care. Designations such as MD, MC and OPS can be used to represent Medicaid, Medicare, Other Payer Source(s) such as a Managed Care Patient respectively. The system can accommodate a plurality of designations or levels of care, preferably about 250, most preferably about 10 to about 50. If data is not entered into any of the available selections, the system simply views these empty categories as a zero.

The system can be configured for census data representing various levels of care and per payer source. Census data includes the number of patients in a facility per care/acuity level. The patients can be further categorized by the levels of care to be provided to the patient. Exemplary categories of care include 1) Intermediate Care, 2) Skilled Care, and 3) Medicare. The system can also be configured to utilize categories to measure per patient day (ppd's)/hour's daily.

Additional exemplary categories include: 1) MD—Intermediate Care, 2) MD—Ventilator Care, 3) MD—Infectious Disease, 4)—Intermediate Care—Specialty Care Unit, 5) MC—Medicare skilled, 6) OPS—a managed care patient who may require additional or different hour requirements from the other residents in a facility.

In step 204, the system receives a facility's budget for clinical hours to be provided to patients. Receiving the clinical hours budget is conducted in the configuring process. Once the data is entered, the clinical hours budget/per care level remain the same until re-set to present different parameters. The budget is determined by a user to meet the user's commercial goals. Once the user has determined the budget for a facility or enterprise, the user can enter the budget into the system. The budget can include total clinical hours of care to be provided in a facility or enterprise. The budget can be based on the actual number of patients per care/acuity level or the estimated number of patients in a facility or enterprise. The budgeted clinical hours can be divided into levels of care as described earlier. The levels of care can range from critical intensive care to supervisory care depending on the level of skilled care required. In one embodiment, the system can default to 2.3 hours/ppd (per patient day) for Intermediate Care (ICF), 2.6 hour/ppd for Skilled Care, 4.0 hours/ppd for Infectious Disease (ID) and Ventilator Care patients. The number of patients can be inputted into the system as well as the requirements or recommended guidelines/allotments/per patient care level/category. In one embodiment, once the user's inputs are saved, the system then allows for two categories of daily input by the user to obtain the systems results—1) that day's resident census (the number of patients) by specific levels of care and 2) the actual clocked payroll hours for the medical staff including licensed nurses and nurses aides. Payroll data and other data can be taken from a time clock or other payroll tracking device. The time clock can be manual or automated in most facilities and in communication with the present system via a distributed computer environment, standard telephony, or wireless communication device. Lastly, the system can also receive monthly census goals (from a recorded patient day standpoint). In one embodiment the system can compute census projections based on the month to date days reported and offer percentage month to date towards the census goals. Once a user inputs the ppd allowable for the desired levels of care, the system automatically computes the total clinical payroll hours. These parameters can be edited or adjusted as needed.

In step 206 the system receives actual clinical hours provided to patients. Actual clinical hours provided can include all payroll hours provided to patients by personnel according to regulatory parameters applicable to that facility. The Actual Hours is data that the system accepts each 24-hours. This data is pulled directly from the time clock of a facility, whether it is pulled manually or automatically. For example, the system can receive this data from Data Terminals 108, by electronically polling time clocks, or by user input. The system can also be adapted to receive clinical hours for personnel outside of the direct-floor caregiver's areas as provided by applicable regulations. This data may be separated during the weekday(s) for 1) clarity, and 2) allow for additional hours of direct clinical floor care hours during the weekday(s).

In step 208 the system processes the data. Data processing includes but is not limited to comparing the actual clinical hours provided to regulatory or recommended guidelines required and budgeted hours. One embodiment of the invention provides comparisons between the actual, budgeted and recommended and/or regulatory requirements each 24-hours (both in total hours and on a ppd basis), based on the pre-set inputs and the daily inputs of 1) the actual clinical hours, and 2) the actual census for that 24-hours/per care level. The system can compute profit/loss, project profit/loss, and determine whether regulatory requirements are being met. The system can suggest levels of care or clinical hours that can be adjusted to meet budget yet maintain regulatory or recommended guidelines compliance.

The system can display the results of the data processing in step 210. The system displays the comparisons mentioned in 208 in numerical and graphical form. The system also displays 'the burn rate' specific to the % of occupancy towards the pre-set census goal based on the existing 'run rate' at that specific time of the month. The desired occupancy/census objectives are inputted at the '202'/configure level. The system can output the results using output device 104. Output device 104 can include a display screen, printer, projector, or other conventional output devices.

In step 212 the system can automatically adjust future allocated clinical hours to meet regulatory requirements. Future allocated clinical hours can be correlated to forecasted census data, preferably per care level. The system can also automatically adjust clinical hours to meet regulatory requirements and budgetary parameters. The system can notify the user that based on received budgetary parameters, regulatory requirements or recommended guidelines will not be met. The system can provide the user with various choices in clinical hour allocations for the user to select. The selected allocations can then be communicated to the facilities in the enterprise. Alternatively, a user can adjust the allocation of resources independently.

Figure 3:
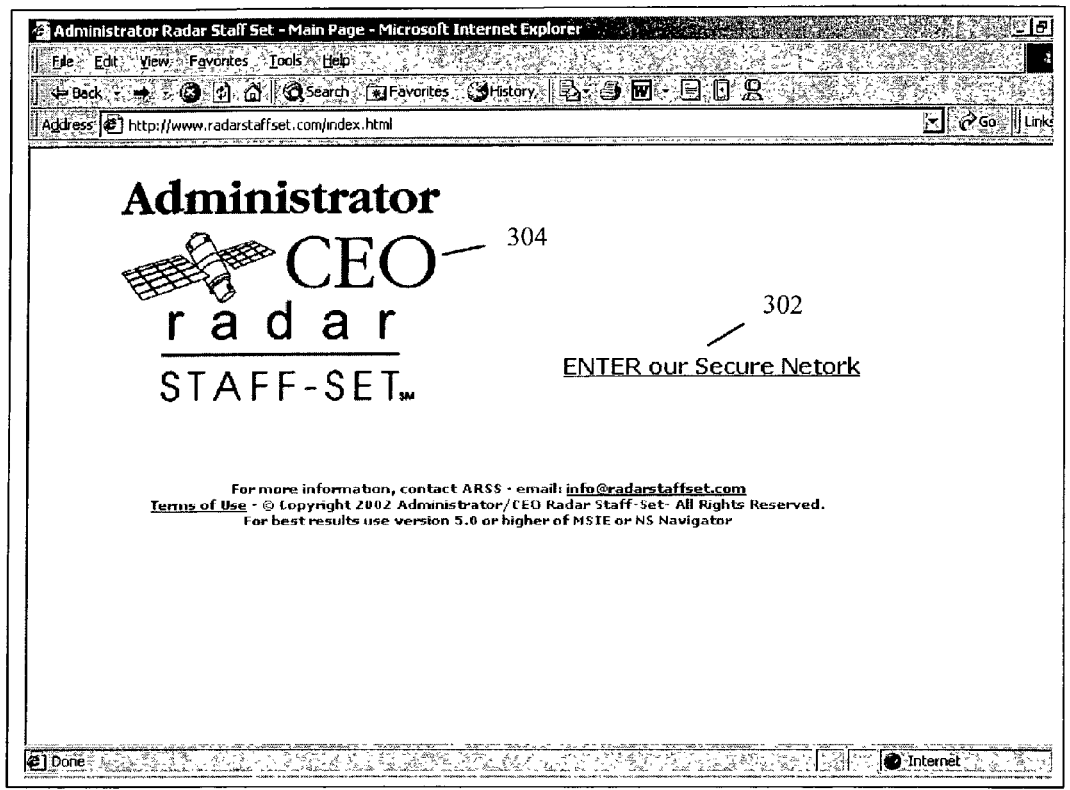
Figure 4:
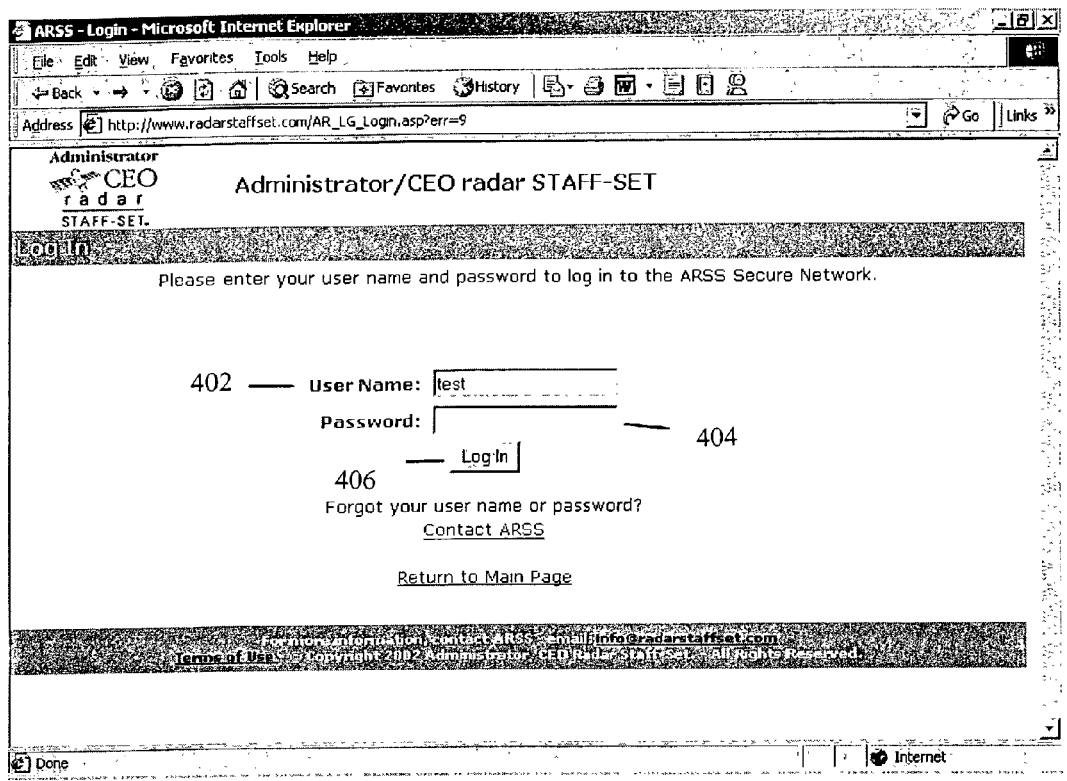
Figure 5:
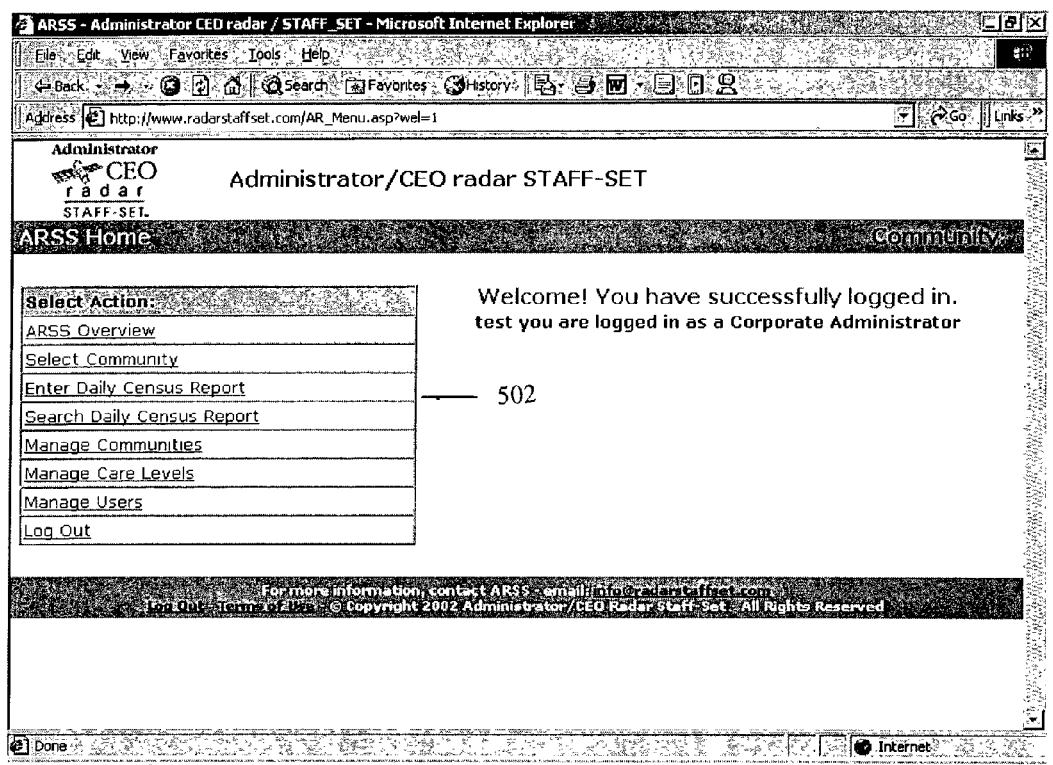
Figure 6:
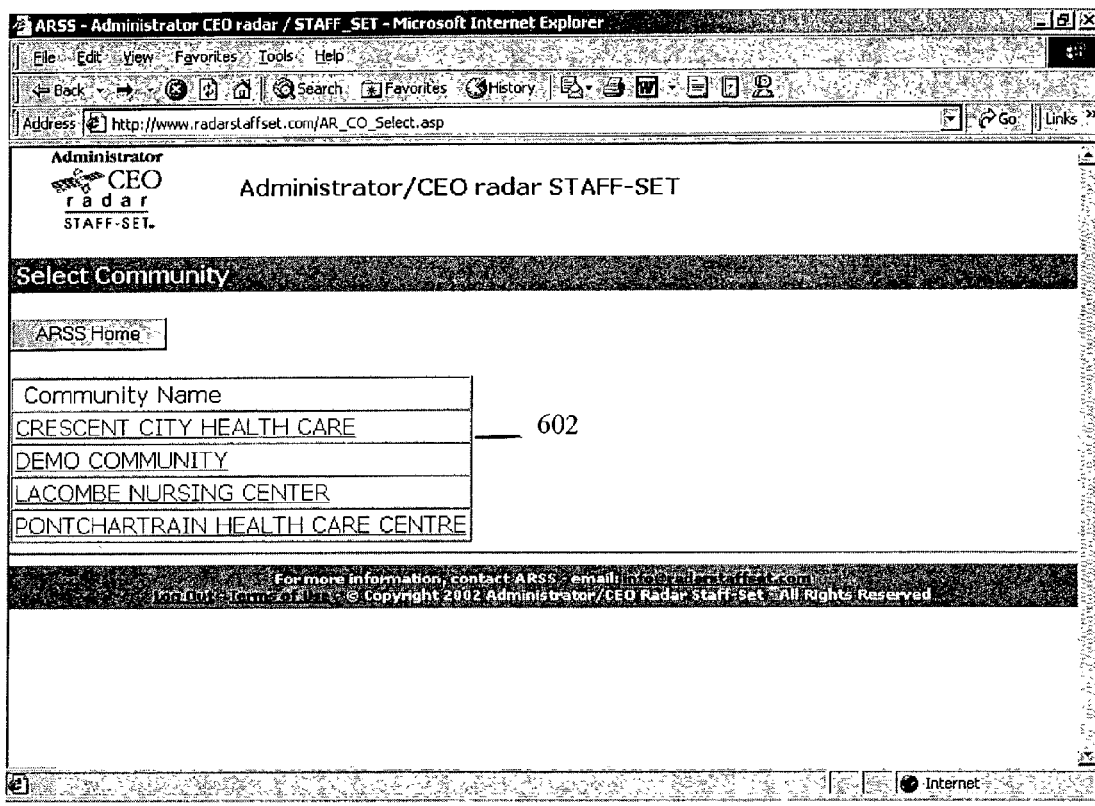

FIG. 3 is an exemplary display screen of an embodiment of the present invention. The display screens can have a home button and other conventional web navigational functions including back, next, forward and the like. The display screens can also comprise web based forms for accepting and processing data. The system can display screen 300 in response to a user accessing the system using IP network 110 with a conventional web browser. Display screen 300 can include a link 302. Link 302 is a link to subsequent web pages of the present invention. Display screen 300 can also include a logo 304. Logo 304 can be used to advertise the system or can be used to advertise any product or service.

In response to a user selecting link 302, the system advances to exemplary display screen 400. Display screen 400 can be a web based form for accepting a user name 402 and a password 404. The user name 402 and password 404 can be alphanumeric characters or symbols. Once the user name and password have been entered, the user can click on button 406 to submit the data to the system.

When the system receives the log in data, the system advances to exemplary display screen 500. In this display screen, the system provides the user with a menu 502 of options. The options can be links to various functions of the system. Exemplary links include links to an overview of the system, select a community or facility, enter data, search data, manage communities or facilities, manage care levels, manage users, or log out. If the user selects the link to an overview of the system, the system can display information describing the system and associated functions. The display can be multimedia including video and audio data as well as graphical and textual data.

In response to a user selecting the link to manage communities, the system advances to exemplary display screen 600. Screen 600 can provide the user with a menu containing links for existing communities or facilities. When a user selects a link, the system advances to a web page for the community or facility associated with that link.

Figure 7A:
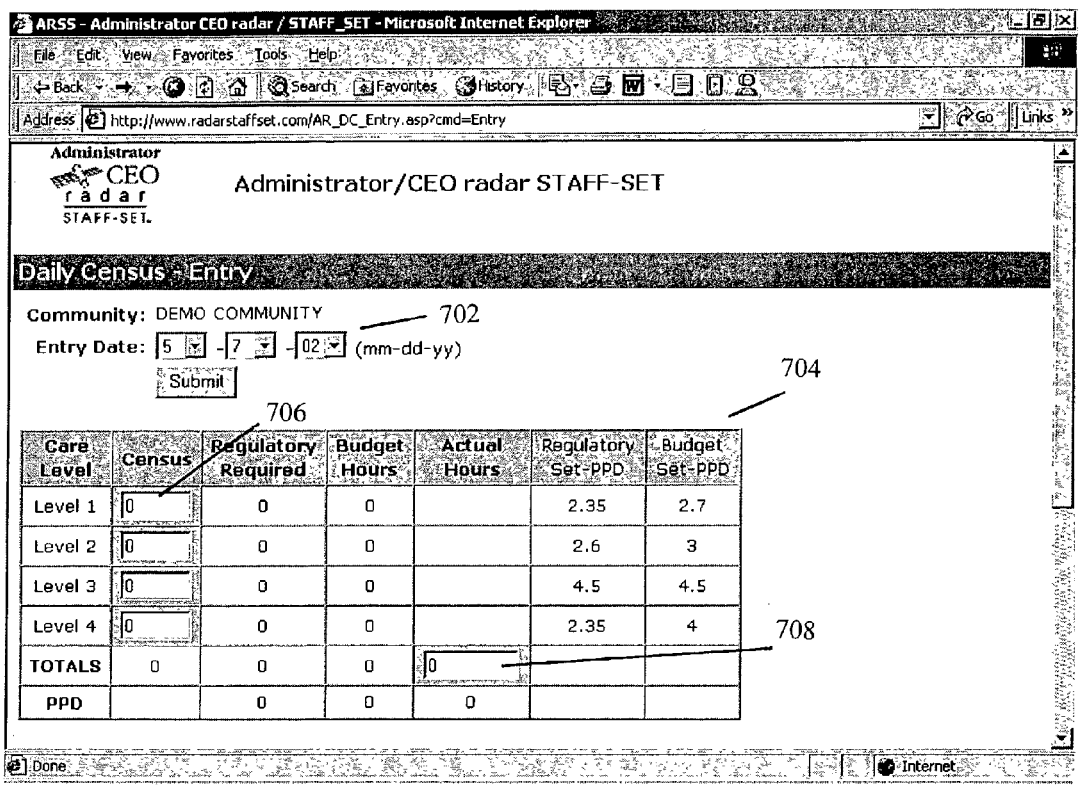
Figure 7B:
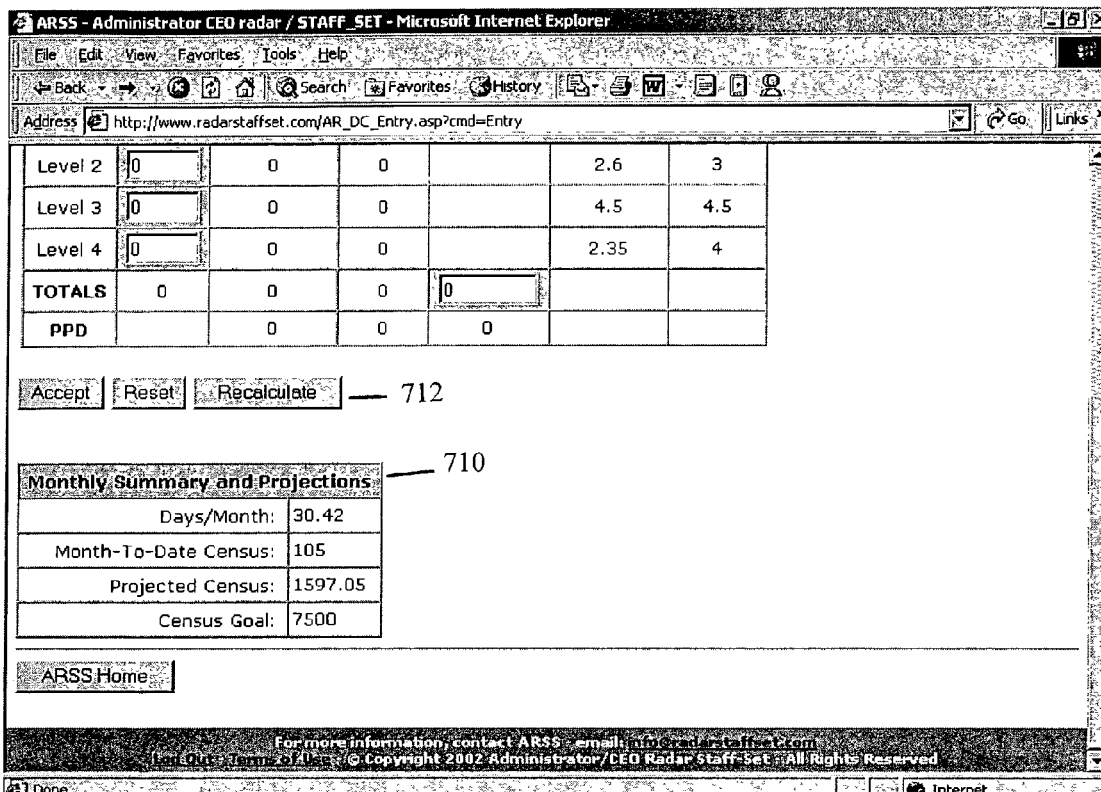
Figure 9A:
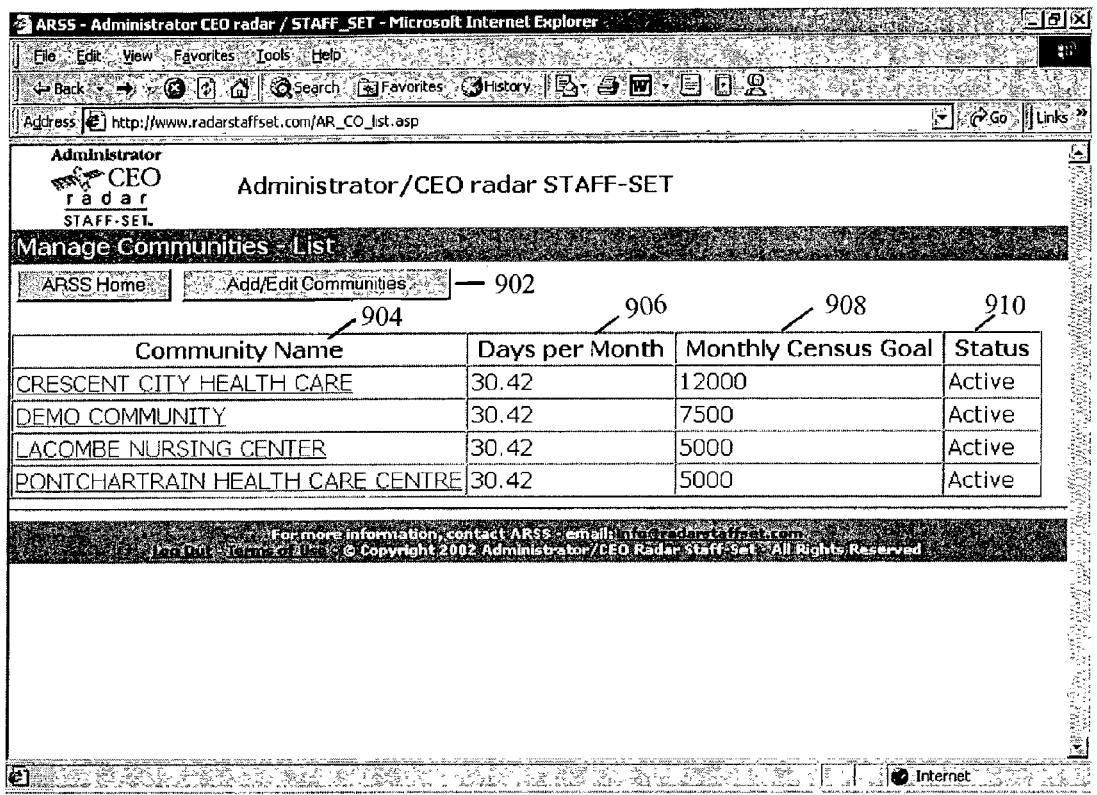
Figure 9B:
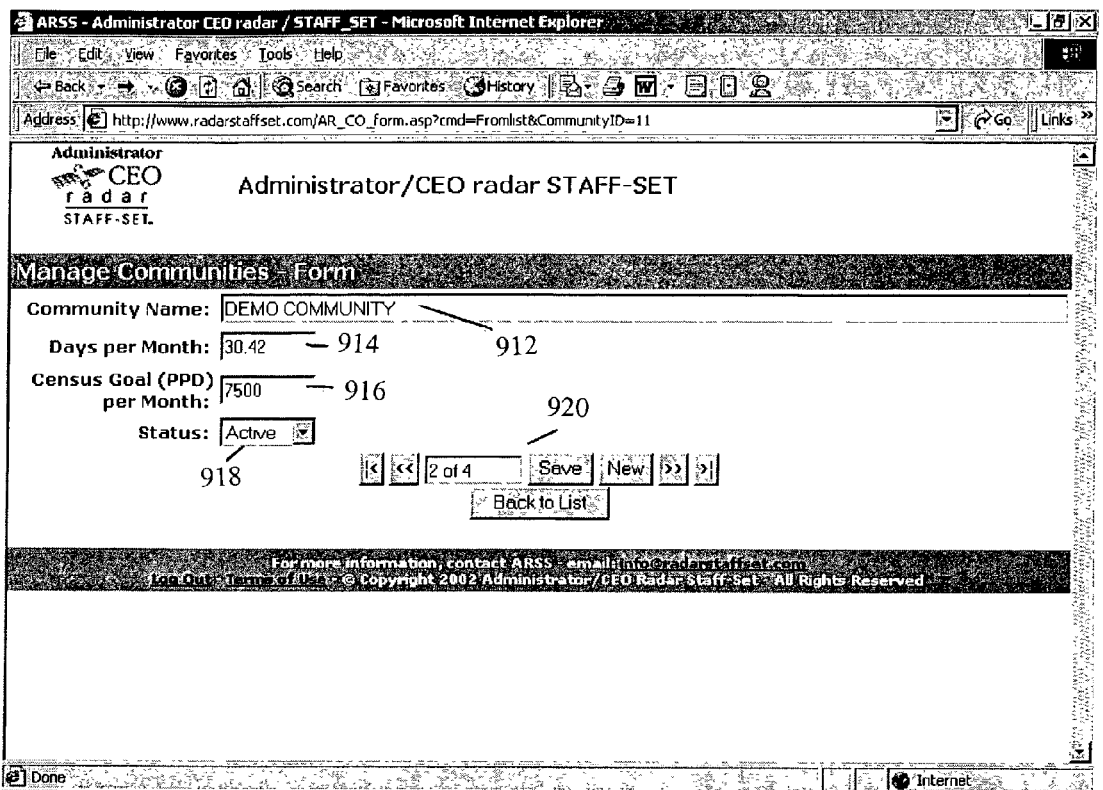
Figure 10A:
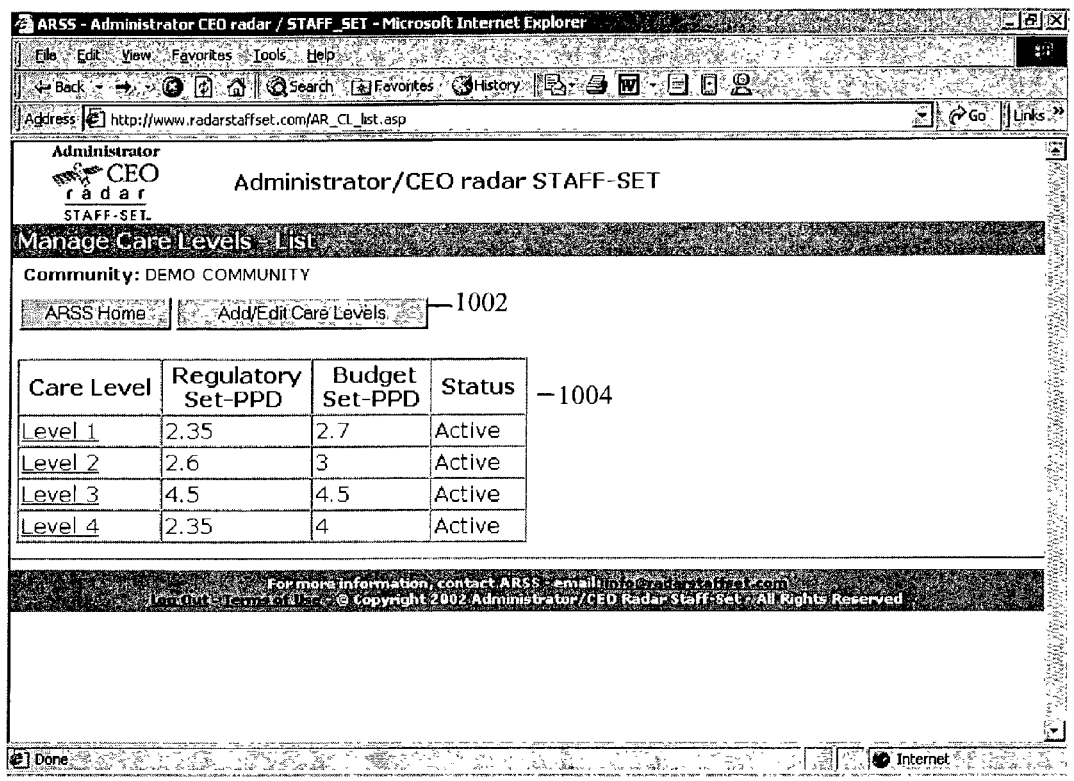
Figure 11A:
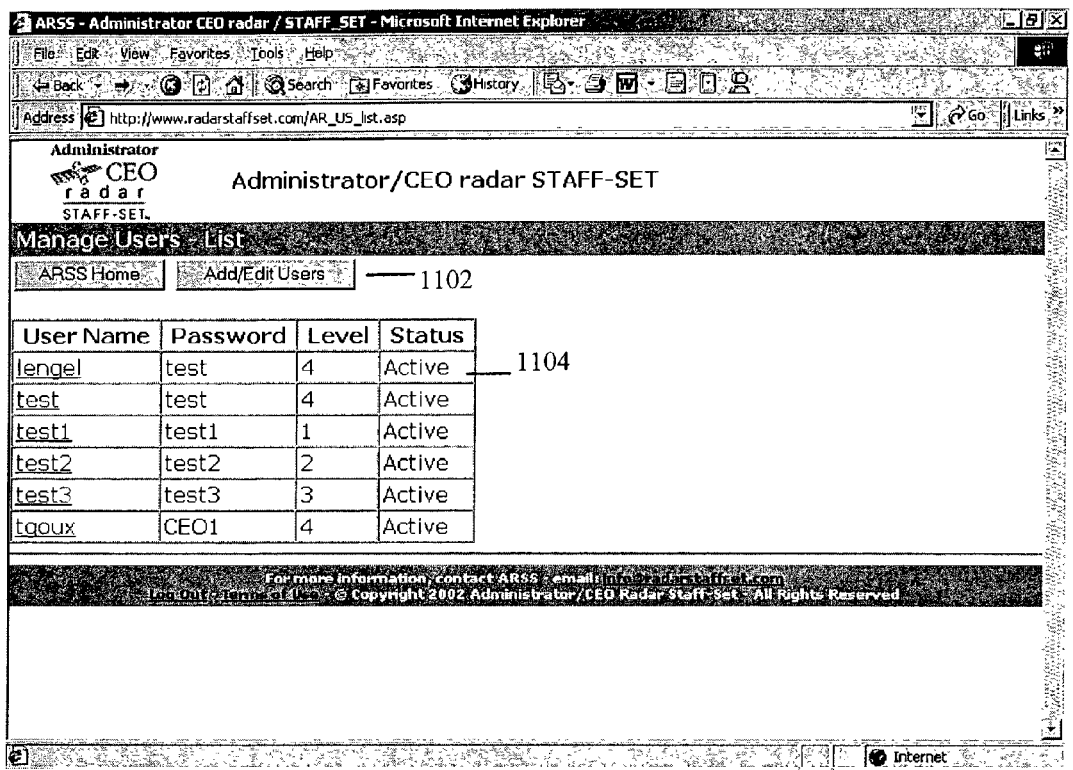
Figure 12:
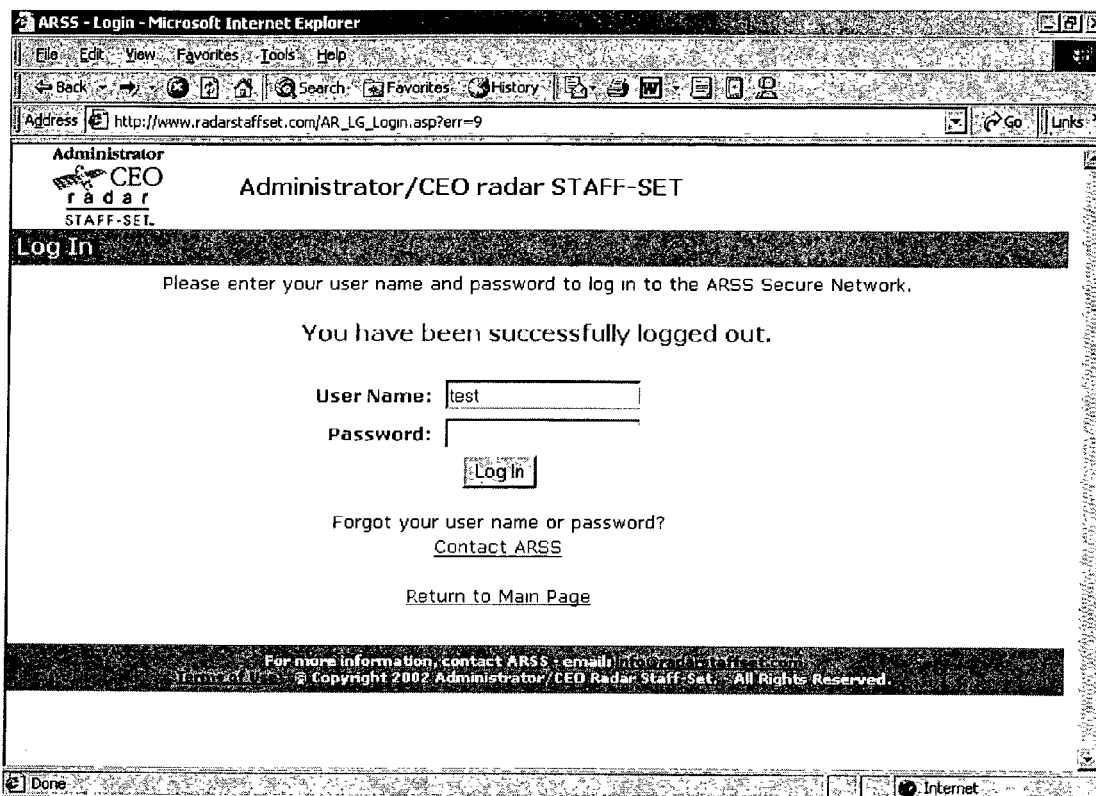

FIG. 7A is an exemplary display screen for a facility that can be used to enter data defining the number of patients in a defined category of care in a selected facility or community. Screen 700A can be displayed in response to a user selecting a link to enter data on screen 500, for example by selecting the link to enter daily census data. Screen 700A contains a drop down menu 702 for entering the date for the corresponding data to be entered. The data is entered into table 704. Table 704 includes blocks 706 for entering the number of patients according to associated levels of care. Block 708 can be used to enter the total number of clinical hours provided for the facility.

Screen 700B is a continuation of screen 700A seen by scrolling downward. Buttons 712 can be used to accept, reset, or recalculate values using inputted data. Results are displayed in table 710 and include cumulative, projected, and actual data as well as budget goals.

If a user selects the link for searching daily census report on display screen 500, the system displays exemplary screen 800. Display screen 800 optionally contains a drop down menu 702 for selecting a data to review data corresponding to that data. Alternatively, a date can be entered using alphanumeric data. The processed data is displayed in table 704 without data entry blocks 706 and 708. Results of the data processing are displayed in table 710.

As user can add or edit communities or facilities in the system by selecting the link to manage communities on display screen 500. In response, the system displays exemplary screen 900A. In the manage communities screen, a user can select button 902 to add or edit a facility. A list containing links to data for existing communities and facilities is provided in column 904. The days in the month can be displayed in column 906. Monthly census goals are displayed in column 908 and the status of the facility or community can be displayed in column 910.

In response to selecting button 902, the system displays exemplary screen 900B. Screen 900B enables a user to edit or create a facility or community. The name of the community can be entered in block 912. The days in a month can be entered in block 914. The census goal of patients per day can be entered in block 916. The status of the facility can be entered in block 918, preferably by using a drop down menu. Finally, navigation buttons 920 can be presented by the system to assist the user in navigating the list of communities or facilities.

A user can edit or create care levels by selecting the corresponding link on display screen 500. In response, the system displays exemplary screen 1000A. Screen 1000A includes a button 1002 that enables the user to edit or add care levels for a community or facility. Currently available care levels are displayed in table 1004. Table 1004 can contain columns listing available care levels, regulatory clinical hours per patient per day, budgeted clinical hours per patient per day, and the status of the care level.

The system displays exemplary screen 1000B in response to a user selecting edit button 1002. Screen 1000B provides the user with a form to add or change care levels for a facility. Block 1006 is displayed to accept a care level designation. The regulatory required or recommended guideline clinical hours can be entered in block 1008, and the budgeted clinical hours for the specified level of care can be entered in block 1010. A user can activate or deactivate a care level by changing the status to active or inactive in block 1012. Buttons 1014 can be used to navigate the list of care levels displayed in screen 1000A.

The system can also be configured to allow users different levels of access. Exemplary levels of user access can be read-only or read and edit. Different functions of the system can require different levels of access. For example one user can be granted rights to enter census date, other users can be granted rights only to read processed data. Different facilities can have different users with different levels of access. In screen 1100A the system can display an edit button 1102 and table 1104. Table 1104 can display a list of users, passwords, access levels, and the status of the user.

In response to a user selecting edit button 1102, the system displays screen 1100B. Screen 1100B can be a form for receiving data from a user for creating users with various levels of system access. A user name can be received in block 1106, and a password can be received in block 1108. The level of access for a specific user can be designated in block 1110.

Table 1114 can list the available communities or facilities. Table 1114 can also have selection box that can be selected to indicate which communities or facilities are activated for a user. Navigation buttons 1116 can be used to assist a user navigate a list of users.

If a user selects the link to log out in display screen 500, the system will then display a system home page or log in screen 1200.

What is claimed is:

1. A healthcare facility management system comprising:
   a data terminal at a healthcare facility located in a geographic location having regulatory required hours of care to be provided to a patient per day based upon the acuity level of the patient; and
   a management control unit having a processor, the processor configured to:
      receive patient census data indicating the total number of patients present in the facility and the acuity level of each patient;
      compute a census projection for a predetermined period of time based upon received patient census data;
      calculate total budgeted clinical hours for the facility from the patient census data and a predetermined number of hours of care to be provided to a patient per day based upon the acuity level of the patient;
      automatically determine total required clinical hours for the facility from the patient census data and the regulatory required number of hours of care to be provided to a patient per day based upon the acuity level of the patient;
      monitor clinical hours provided at the facility;
      compare clinical hours provided at the facility to total clinical hours budgeted to project a deficit or surplus between total actual clinical hours provided and total budgeted clinical hours;
      compute a burn rate based upon at least the total clinical hours budgeted and actual clinical hours provided, the burn rate indicating a rate of revenue loss or gain;
      compute projected profit or loss for the facility for the predetermined period of time based upon at least the burn rate and the census projection;
      compare clinical hours provided at the facility to total required clinical hours to project a deficit or surplus between total actual clinical hours provided and total required clinical hours; and
      provide a staffing schedule adjustment recommendation based upon the projected profit or loss and a comparison of clinical hours provided and projected deficit or surplus such that: actual clinical hours provided will be no greater than the total clinical hours budgeted and no less than the total required clinical hours for each facility; and a computation based upon at least the adjusted staffing schedule and the census projection will indicate a profit for the facility.

2. A computer readable medium having program instructions tangibly stored thereon executable by a processor to perform a method for managing clinical hours in a regulated inpatient healthcare facility, the method comprising:
   receiving patient census data indicating the total number of patients present in a healthcare facility and the acuity level of each patient;
   determining the total required clinical hours mandated by regulations to be provided by the facility during a predetermined period of time based upon the patient census data;
   receiving total budgeted clinical hours for the facility for the predetermined period of time;
   monitoring in real-time actual clinical hours provided at the healthcare facility;
   calculating the projected actual clinical hours provided during the predetermined period of time based upon the monitored real-time clinical hours provided and total budgeted clinical hours;
   generating a warning if the projected actual clinical hours are below the total required clinical hours; and
   computing projected profit or loss for the facility for the predetermined period of time based upon at least the total clinical hours budgeted and actual clinical hours provided;
   providing a staffing schedule adjustment recommendation such that the projected actual clinical hours are less than or equal to total budgeted clinical hours and greater than or equal to the total required clinical hours.

3. A computer readable medium having program instructions tangibly stored thereon executable by a processor to perform a method for managing clinical hours in a regulated inpatient healthcare facility, the method comprising:
   receiving current patient census data indicating the total number of patients present in a healthcare facility and the acuity level of each patient;
   receiving a census goal for a predetermined period of time;
   computing a census projection for the predetermined period of time based upon received patient census data;
   computing projected profit or loss for the facility for the predetermined period of time;
   determining the total required clinical hours mandated by regulations to be provided by the facility during the predetermined period of time based upon the census projection;
   receiving total budgeted clinical hours for the facility for the predetermined period of time;
   monitoring in real-time actual clinical hours provided at the healthcare facility;
   calculating the projected actual clinical hours provided during the predetermined period of time based upon the monitored real-time clinical hours provided and total budgeted clinical hours;
   computing a burn rate based upon at least the received total actual hours provided and total budgeted clinical hours, the burn rate indicating a rate of revenue loss or gain;
   computing profit or loss for the facility for the predetermined period of time based upon at least the burn rate;
   generating a warning if the projected actual clinical hours are below the total required clinical hours; and
   providing a staffing schedule adjustment recommendation such that the projected actual clinical hours are less than or equal to total budgeted clinical hours and greater than or equal to the total required clinical hours.

* * * * *